US008349573B2

(12) United States Patent
Wan et al.

(10) Patent No.: US 8,349,573 B2
(45) Date of Patent: Jan. 8, 2013

(54) METHODS AND DEVICE FOR THE DETECTION OF OCCULT BLOOD

(76) Inventors: John Wan, San Marino, CA (US); Zhijing Wan, Beijing (CN)

( * ) Notice: Subject to any disclaimer, the term of this patent is extended or adjusted under 35 U.S.C. 154(b) by 0 days.

(21) Appl. No.: 13/222,576

(22) Filed: Aug. 31, 2011

(65) Prior Publication Data
US 2011/0318228 A1 Dec. 29, 2011

Related U.S. Application Data

(62) Division of application No. 11/978,820, filed on Oct. 30, 2007, now Pat. No. 8,053,203.

(51) Int. Cl.
*G01N 31/00* (2006.01)
*G01N 33/53* (2006.01)

(52) U.S. Cl. ............ 435/7.21; 435/7.1; 436/1; 436/501; 436/518; 424/9.1; 424/520; 422/50; 530/300; 530/350

(58) Field of Classification Search .................. None
See application file for complete search history.

(56) References Cited

U.S. PATENT DOCUMENTS

| | | | |
|---|---|---|---|
| 4,313,734 A | 2/1982 | Leuvering | |
| 4,920,045 A | 4/1990 | Okuda et al. | |
| 5,266,497 A | 11/1993 | Imai et al. | |
| 5,521,102 A | 5/1996 | Boehringer et al. | |
| 5,543,115 A | 8/1996 | Karakawa | |
| 6,020,147 A | 2/2000 | Guire et al. | |
| 6,352,862 B1 | 3/2002 | Davis et al. | |
| 6,410,336 B1 | 6/2002 | Augurt | |
| 6,485,982 B1 | 11/2002 | Charlton | |
| 6,528,325 B1 | 3/2003 | Hubscher et al. | |
| 7,241,417 B2 | 7/2007 | Lee et al. | |
| 2002/0072596 A1 | 6/2002 | Ruben et al. | |
| 2002/0076820 A1 | 6/2002 | Craine | |
| 2003/0149256 A1 | 8/2003 | Ruben et al. | |
| 2008/0227208 A1* | 9/2008 | Yee et al. | ........................ 436/66 |

FOREIGN PATENT DOCUMENTS

| | | | |
|---|---|---|---|
| CN | 1465977 A | 1/2004 | |
| CN | 1182392 C | 12/2004 | |
| CN | 2876780 Y | 3/2007 | |
| CN | 200953022 Y | 9/2007 | |
| CN | 200956029 Y | 10/2007 | |
| EP | 0123868 A2 | 11/1984 | |
| EP | 0696735 A1 | 2/1996 | |
| EP | 1742051 | * | 2/2001 |
| EP | 1256802 A1 | 11/2002 | |
| EP | 1621886 A1 | 2/2006 | |
| EP | 1742051 A2 | 1/2007 | |
| JP | 60-89756 A | 5/1985 | |
| JP | 10-221338 | 8/1998 | |
| JP | 2002-530651 A | 9/2002 | |
| JP | 2008-522196 A | 6/2008 | |
| WO | 00/29852 A1 | 5/2000 | |
| WO | 01/61343 A1 | 8/2001 | |
| WO | 20061062800 A1 | 6/2006 | |

OTHER PUBLICATIONS

Miyoshi et al. ("Clinical study of a new fecal occult blood test using a combination assay of hemoglobin and transferrin," Gastroenterologia Japonica. vol. 26, No. 2 (1991), p. 151-156).*
Chiang et al. Kaohsung Journal of Medical Science., May 2006, vol. 22, No. 5 pp. 223-228.*
Maggio (Immunoenzyme technique I, CRC press â 1980, pp. 186-187).*
Chiang, C. et al., "A Comparative Study of Three Fecal Occult Blood Tests in Upper Gastrointestinal Bleeding" The Kaohsiung Journal of Medical Sciences (May 2006) pp. 223-228, vol. 22, No. 5.
Miyoshi, H. et al, "Immunological Determination of Fecal Hemoglobin and Transferrin Levels: A Comparison with Other Fecal Occult Blood Tests" The American Journal of Gastroenterology (1992) pp. 67-73, vol. 87, No. 1.
Supplementary European Search Report dated Feb. 28, 2011.
Miyoshi, H. et al., "Accuracy of Detection of Colorectal Neoplasia Using and Immunochemical Occult Blood Test in Symptomatic Refered Patients: Comparison of Retrospective and Prospective Studies" Internal Medicine (2000) pp. 701-706, vol. 39, No. 9.
Maggio, Immunoenzyme Technique 1 (1980) CRC Press, pp. 186-187.
Miyoshi, H. et al., "Clinical Study of a New Fecal Occult Blood Test Using a Combination Assay of Hemoglobin and Transferring" Gastroenterologia Japonica (1991) pp. 151-156, vol. 26, No. 2.
Official Action dated Jan. 4, 2012 received from the Japanese Patent Office in Japanese Patent Application No. JP 2010-532100, together with English-Language translation.
Fie, W., ''The Effect of Transferrin Detecting in Digestive Tract Hemorrhage Detection Rate Chinese Journal of Medical Instrumentation (2011) pp. 462-464, vol. 35, No. 6, together with English-language abstract.
Li, M.Y. et al., "Application of Fecal Occult Blood Detected by Transferrin/Hemoglobin Colloidal Gold Method" Lab. Med. Clin. (Jul. 2010) pp. 1459-1460, vol. 7, No. 14, together with English-language abstract. Official Action dated Oct. 23, 2012 received from the Chinese Patent Office in Chinese Patent Application No. CN 200880123614.1.

* cited by examiner

*Primary Examiner* — Lisa Cook

(74) *Attorney, Agent, or Firm* — Scully, Scott, Murphy & Presser, P.C.

(57) ABSTRACT

The present invention relates generally to detection of occult blood. In particular, the present invention provides a device and methods for the simultaneous detection of hemoglobin and transferrin in fecal samples, which permit a more sensitive diagnosis of occult blood in fecal sample and a differential diagnosis of bleeding of the upper GI tract versus the lower GI tract.

4 Claims, 2 Drawing Sheets

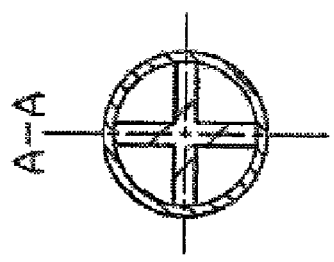
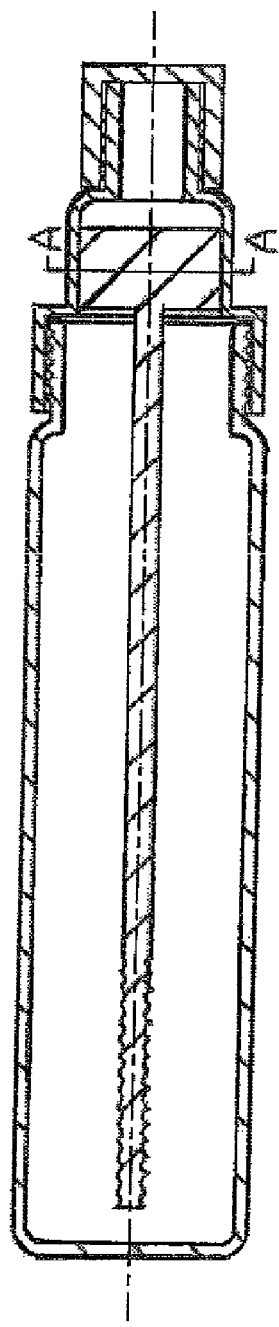
Figure 1B
Figure 1A

METHODS AND DEVICE FOR THE DETECTION OF OCCULT BLOOD

CROSS REFERENCE TO RELATED APPLICATION

This application is a divisional of U.S. patent application Ser. No. 11/978,820, filed Oct. 30, 2007 now issued U.S. Pat. No. 8,053,203 the entire content and disclosure of which is incorporated herein by reference.

FIELD OF THE INVENTION

The present invention relates generally to detection of occult blood from samples of the gastrointestinal (GI) tract. In particular, the present invention provides a device and methods for the detection of transferrin, or alternatively, the simultaneous detection of hemoglobin and transferrin, using GI samples. The methods of the present invention provide a basis for the diagnosis of GI bleeding, and a basis for a differential diagnosis of bleeding from the upper GI tract versus the lower GI tract.

BACKGROUND OF THE INVENTION

Fecal occult blood ("FOB") is a good indicator for monitoring bleeding from the gastrointestinal (GI) system. Since it may take several years for some colon polyps to transform into colorectal cancers, the detection of bleeding colon polyps is an effective way to screen for colorectal cancer at an early stage. The implementation of a procedure to screen for occult blood in fecal samples for adults of 50 years or older has reduced the incidences of colorectal cancer by 20% and mortality by 30%.

Currently available FOB tests include a chemical test that detects hemoglobin metabolites in fecal samples. The test employs an oxidizable substrate (such as guaiac) that produces a colored product in the presence of peroxide and hemoglobin. Since most animal heme molecules, plant ingredients and common vitamins can also catalyze the hydrogen peroxide reaction, diet control is critical to specificity of this type of chemical test. A strict diet control poses a serious patient compliance problem. On average, a compliance rate of lower than 10% is not unusual. Further, chemical tests generally have a limited sensitivity. For example, a FOB test using guaiac as substrate has a test sensitivity of 50 µg/ml, with an improved version having a test sensitivity of 20 µg/ml.

A sandwich immunoassay for hemoglobin has been developed, which provides improved test sensitivity and specificity as compared to chemical tests. The need for diet control is also eliminated for such immunoassay.

Hemoglobin is a labile protein; it degrades rapidly in human GI system. Hemoglobin is also susceptible to degradation during shipping and storage after fecal samples are collected. All these sample degradation problems affect the test accuracy of hemoglobin assays.

Transferrin is another biomarker for detecting fecal occult blood. In normal human blood the concentrations of transferrin and hemoglobin are 3 mg/ml and 150 mg/ml, respectively. On the other hand, the hemoglobin versus tranferrin ratio in fecal samples is approximately 5, which is much lower than the ratio (approximately 50) in blood. This observation indicates that transferrin is about 10 times more stable than hemoglobin in the GI tract. It has been reported that certain diseases may affect the levels of transferrin in blood and fecal samples to the extent that an FOB test based on transferrin alone may produce false negative results. A combination test for detecting both hemoglobin and transferrin may improve test sensitivity without sacrificing test specificity.

Another challenge for developing an FOB assay is that very few automated analyzers currently on the market can handle fecal samples. Therefore, a rapid onsite FOB test is desirable and in demand.

SUMMARY OF THE INVENTION

The present invention provides an immunoassay method and device that can detect bleeding from the entire GI system, and can support a differential diagnosis of upper GI bleeding versus lower GI bleeding. The immunoassay of the present invention involves detection of transferrin alone, or alternatively, the simultaneous detection of hemoglobin and transferrin, using GI samples.

In one aspect, the present invention provides a method for detecting transferrin in an upper GI sample to aid in the diagnosis of bleeding from the upper GI tract. Upper GI samples include vomited materials or materials collected from the stomach, for example.

In another aspect, the present invention provides a method for the simultaneous detection of hemoglobin and transferrin in fecal samples to aid in the diagnosis of bleeding from the GI tract, and to differentiate bleeding in the upper GI tract from bleeding in the lower GI tract.

In one embodiment, the present invention provides a method for detecting fecal occult blood by detecting transferrin and hemoglobin in a fecal sample, and comparing the amounts of transferrin and hemoglobin detected with the respective predetermined values, thereby determining the presence or absence of occult blood in said sample.

In a specific embodiment, a detection result is indicative of bleeding from the lower GI tract when both transferrin and hemoglobin test positive, in other words, the amount of transferrin in the fecal sample is above a predetermined value of transferrin and the amount of hemoglobin in the sample is also above a predetermined value of hemoglobin.

In another embodiment, a detection result is indicative of bleeding from the upper GI tract when transferrin tests positive and hemoglobin tests negative, in other words, the amount of transferrin in the sample is above a predetermined value for transferrin and the amount of hemoglobin in the sample is below a predetermined value for hemoglobin.

In still another embodiment, if both transferrin and hemoglobin test negative using a fecal sample, such a result is indicative of no bleeding of the entire GI tract.

According to the present invention, the detection of transferrin and hemoglobin can be achieved by a variety of assays. In one embodiment, the detection is achieved by sandwich immunoassay, which employs a complementary pair of anti-transferrin antibodies and a complementary pair of anti-hemoglobin antibodies.

In a specific embodiment, the detection of transferrin and hemoglobin is achieved using a lateral flow sandwich immunoassay device.

In one embodiment, the lateral flow device suitable for use in the present invention contains a test strip. The test strip contains a solid support, and a test membrane is placed on top of the support. On the top surface of the test membrane are areas where reagents are immobilized, including a test zone containing two separate sites, one of which is immobilized with an anti-transferrin antibody, and the other is immobilized with an anti-hemoglobin antibody; and a control site wherein a control antibody (such as a goat anti-mouse antibody) is immobilized thereto. Additionally, the test strip contains a sample pad, a conjugate pad, and an absorption pad.

The sample pad is placed in contact with and upstream of the conjugate pad, which, in turn, is placed in contact with an end portion of the testing membrane. The absorption pad is placed on top of the other end portion of the testing membrane. The conjugate pad contains a labeled anti-transferrin antibody and a labeled anti-hemoglobin antibody, and is placed upstream of the test zone. Preferably, the test membrane is made of nitrocellulose; and the labeled anti-transferrin antibody and said labeled anti-hemoglobin antibody are both antibodies conjugated to gold particles.

In another embodiment, the lateral flow device suitable for use in the present invention contains two test strips, one for testing hemoglobin and the other for testing transferrin.

In a further aspect, the present invention provides a lateral flow immunoassay device for simultaneous detection of transferrin and hemoglobin in a sample. The sample may be a GI sample or a sample of body fluids.

BRIEF DESCRIPTION OF THE DRAWINGS

FIG. 1A is a fecal sample collection device. FIG. 1B is a sectional view of the device shown in FIG. 1A. The device contains a small screw cap, a large cap with stick and a vial with storage buffer. A user will unscrew the large cap with the brush from the vial, stabbing a fecal sample multi-times at different locations; insert the brush back into vial with storage buffer and tighten the screw. The fecal material collected on the brush will then be re-suspended into storage buffer and ready for testing. When a test operator receives the vial, the operator only needs to unscrew the small cap and squeeze the sample solution directly onto test device.

DETAILED DESCRIPTION OF THE INVENTION

Figure 2:
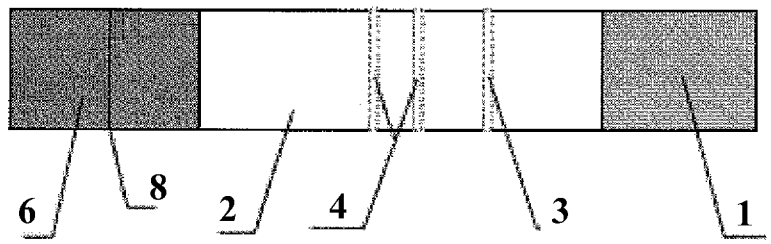
FIG. 2 is a top view of the test membrane for a combination sandwich immunoassay for transferrin and hemoglobin. The test strip includes an absorption pad (1), nitrocellulose membrane (2), a control line (3), two test lines for transferrin and hemoglobin, respectively (4), a marked line for maximum liquid level (8) and a sample pad (6).

The present invention provides a sandwich immunoassay method and device that can detect bleeding from the entire GI system, and can support a differential diagnosis of upper GI bleeding versus lower GI bleeding. The immunoassay involves detection of transferrin alone, or alternatively, the simultaneous detection of hemoglobin and transferrin. The immunoassay of the present invention can utilize GI samples as well as samples of body fluids suspected of containing occult blood.

The present invention is based, at least in part, on the recognition of the difference in stability between transferrin and hemoglobin as occult blood markers. In most upper GI bleeding cases, hemoglobin is completely destroyed by gastric acids and proteases from the stomach, intestine and bacteria. Transferrin, on the other hand, can survive passage through the GI tract. In tests conducted leading to the present invention, it has been found that in patients clinically diagnosed to suffer from an upper GI disorder, transferrin tested positive and hemoglobin tested negative in fecal samples as well as in vomit and liquid samples collected from the upper GI. Additionally, it has been found that in patients clinically diagnosed to suffer from a lower GI disorder where hemoglobin tested positive in fecal samples, transferrin also tested positive.

Accordingly, in one embodiment, the present invention provides a method for detecting transferrin in upper GI samples to aid in the diagnosis of bleeding from the upper GI tract. In another embodiment, the present invention provides a method for the simultaneous detection of hemoglobin and transferrin in fecal samples to aid in the diagnosis of bleeding from the entire GI tract, and to differentiate bleeding in the upper GI tract from bleeding in the lower GI tract. In a further embodiment, test devices are provided for performing the methods of the present invention.

The term "upper GI tract" refers to the upper portion of the GI tract and includes the mouth, pharynx, esophagus, stomach and dodeneum. On the other hand, the "lower GI tract" refers to the lower portion of the GI tract and consists of the intestines, colon, rectum and anus. Although applicable to diagnosis of bleeding from any parts of the GI tract, the presently claimed method is particularly useful for diagnosis of bleeding from the upper GI tract, whereas currently there is no reliable fecal strip-based test available in clinical setting.

The term "GI sample" refers to a sample or collection of solid or liquid materials released or secreted from the GI tract, such as feces and vomits (an upper GI sample), as well as solid or liquid materials collected from the GI tract, such as gastric materials retrieved from the stomach (also an upper GI sample). The raw materials collected are typically suspended or diluted in a buffer (such as saline solutions) before use in an immunoassay.

By "fecal sample" is meant a sample collected following defecation, which is typically mixed subsequently with a solution, which is suitable for use in an immunoassay.

The term "diagnosis" or "diagnosing" should be understood to mean determination of the likelihood of the bleeding being associated with upper or lower GI tract. For example, when transferrin is tested positive in a fecal sample whereas hemoglobin is tested negative, then bleeding is likely to be from the upper GI tract. When both hemoglobin and transferrin are tested to be "positive" in a fecal sample, then bleeding is likely to be from the lower GI tract. Diagnosis can also be made based on the relative ratio of hemoglobin to transferrin in a fecal sample—the higher the ratio (or the closer the ratio is to the ratio in blood), the more likely the test subject has lower GI tract bleeding. Conversely, the lower the ratio, the more likely the test subject has upper GI tract bleeding.

The terms "positive" and "negative" refer to values of a test analyte to be above and below a predetermined value (base or threshold concentration), respectively. The terms also refer to the presence and absence, respectively, of a detectable or visible signal.

The "predetermined value" for an analyte refers to the base or threshold concentration of an analyte in normal individuals; and if the value of the analyte is significantly above such predetermined value, it is indicative of abnormality such as bleeding. The predetermined value for an analyte may vary depending on the format of the assay, and the specific reagents employed in the assay (e.g., the particular antibodies used), but can be determined and set by those skilled in the art by assessing the concentration of the analyte in normal individuals relative to control samples containing known amounts of the analyte.

According to the present invention, hemoglobin and transferrin in GI samples can be detected by a variety of immunoassays using antibodies specific for hemoglobin and transferrin.

By "antibody" is meant a monoclonal or polyclonal antibody. Both full-length antibody molecules and antigen-binding fragments of full-length antibodies can be employed.

In a specific embodiment, the detection is achieved by employing a sandwich immunoassay, which involves the use of a pair of antibodies specific for the analyte to be detected. The antibodies in the pair are complementary to each other—that is, the antibodies bind to different epitopes of the analyte and permits the formation of the sandwich complex: antibody 1-analyte-antibody 2. Typically, one antibody of the antibody pair is immobilized on a solid material (also referred to as "capture antibody"), for example, on a nitrocellulose membrane, a microtiter plate, or beads, whereas the other antibody of the pair is conjugated with a label or a signal generator. To perform the assay, a sample containing the analyte is mixed with the antibody conjugate to form a reaction mixture, and the reaction mixture is then applied to the solid material, permitting the capture antibody to capture of complex formed between the analyte and antibody conjugate. Alternatively, a sample containing the analyte is applied to the solid material and is captured by the capture antibody bound to the solid material. A conjugate antibody is then added to form a sandwich complex between the capture antibody, the analyte and the conjugate antibody. Unbound materials are washed away, and a signal is developed and read, either visually or instrumentally.

According to the present invention, an antibody can be conjugated to a "label", "signal generator" or "signal generating element" (hence also referred to as a "labeled antibody"), which refers to an entity that can embody a number of different forms: enzymes and their resultant effects on a substrate, colloidal metal particles, and latex with dye incorporated, and dye particles. An enzyme can react on a substrate to produce a product that is sensible, for example, by color of absorption (e.g., ultraviolet, visible, infrared), or by fluorescence.

In one embodiment of the present invention, metal particles are employed as signal generator, which can be made of platinum, gold, silver, selenium, or copper or any other of metal compounds which exhibit characteristic colors. The metal particles suitable for use in the present invention can be prepared by conventional methodologies. For example, the preparation of gold sol particles is described Frens, *Nature* 241: 20-22 (1973). Additionally, the metal particles may be metal or metal compounds or polymer nuclei coated with metals or metal compounds, as described in U.S. Pat. No. 4,313,734.

In a preferred embodiment, the metal particles are gold particles of a size in the range of 5 nm to 100 nm, preferably in the range of 8 nm to 60 nm, and more preferably in the range of 10 to 40 nm.

A desired antibody can be coupled to metal particles using conventional techniques, including but not limited to covalent coupling and hydrophobic bonding. Additionally, the antibody can be conjugated to the particles using a biotin/streptoavidin linkage.

Additionally, other solid phase particles suitable for use in producing particles conjugated with antibodies include, for example, particles of color latex, carbon black and dye particles.

Figure 3:
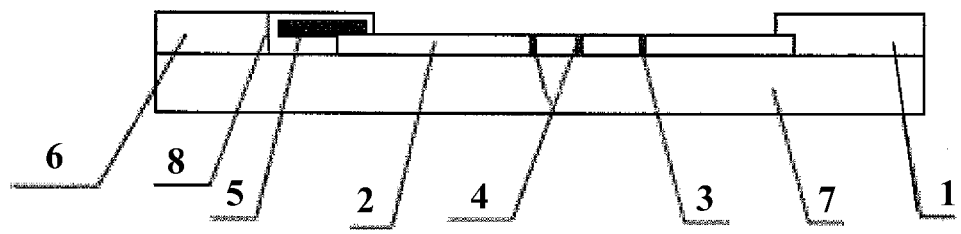
FIG. 3 is a cross section of the same strip where item 7 is a plastic backing and item 5 is a gold-antibody conjugate pad underneath a label.
Figure 4A:
FIGS. 4A-4C illustrate three possible versions for a positive result of the presence of blood in the fecal sample.
Figure 4B:
Figure 4C:

In another specific embodiment, the detection of hemoglobin and transferrin is achieved by employing a lateral flow immunoassay. A device illustrating the working of such an assay is shown in FIGS. 2-3.

The immunoassay lateral flow test device generally includes a test strip having a backing support 7, which can be made of plastic, cardboard, or any other rigid material, and preferably made of a plastic material. On top of the backing support 7, is a testing membrane 2, preferably made of a nitrocellulose membrane, which may be affixed to the support 7. On the top surface of the testing membrane 2 are the areas to which the appropriate reagents are affixed, including a test area 4 comprising two separate test sites, with an anti-transferrin antibody immobilized to one site, and an anti-hemoglobin antibody immobilized to the other site. The testing membrane also has a control zone 3 having a control antibody immobilized thereto.

The test strip also contains a sample site for applying a diluted sample to the test strip, and a conjugate site downstream of the sample site. Generally, an absorbent sample pad 6 is placed at the sample site, and is placed in contact with a conjugate pad 5 at the conjugate site. The conjugate pad is typically placed on top of and in direct contact with one end portion of the testing membrane 2, and contains an anti-transferrin antibody conjugated with a signal generating element and an anti-hemoglobin antibody also conjugated with a signal generating element. At the other end of the test membrane 2 and on top of the testing membrane is placed an absorption pad 1. When a GI sample is applied to the sample pad 6, the sample will migrate towards the absorption pad 1 and get transferred to the test membrane 2.

In a specific embodiment, the conjugate site is a pad containing gold particles conjugated with an antitransferrin antibody and gold particles conjugated with an anti-hemoglobin antibody. Gold particles conjugated with an antibody can be prepared as described above, and are preferably of a size in the range of 5 nm to 100 nm, more preferably in the range of 8 nm to 60 nm, and even more preferably in the range of 10 to 40 nm.

As described above, other metals (such as platinum, silver, selenium, and copper) can also be used to produce metal particles conjugated with an antibody. Additionally, other solid phase particles suitable for use in producing particles conjugated with antibodies include, for example, particles of color latex, carbon black and dye particles.

In one embodiment, the gold antibody conjugates are deposited and dried on a absorbent pad 5, which is placed downstream from the sample pad 6 where the sample is applied. In an alternative embodiment, gold particles conjugated with a desired antibody are dried and deposited directly on the end of test membrane 2 adjacent and downstream of the sample pad 6.

The lateral flow immunoassay device illustrated in FIGS. 2-3 can also include a casing, in which the test strip is placed. The casing can take a number of different forms that permit the application of the sample to the sample pad, permit the sample to migrate along the test membrane by lateral flow, and permit the viewing the results that occur in the test and control zones.

Figure 5:
FIG. 5 illustrates a negative result with the combination test.
Figure 6:
FIG. 6 shows that in the absence of a colored control line the test result is invalid.

FIGS. 2-5 illustrate the assembly of a test strip for a simultaneous detection of transferrin and hemoglobin based on sandwich immunoassays. A GI sample is applied onto the sample pad 6, and the liquid in the sample migrates by capillary action towards the absorption pad 1. When the liquid sample reaches the gold conjugate pad 5, the gold-anti-transferrin conjugate and gold-anti-hemoglobin conjugate within the gold conjugate pad 5 are resuspended in the liquid, and the resulting complexes, i.e., gold-anti-transferin-transferin and gold-anti-hemoglobin-hemoglobin, then move onto the membrane 2. When the liquid sample containing the complexes reaches the test zone 4, it will react with the anti-transferrin and anti-hemoglobin antibodies immobilized on their respective test line. In the absence of a specified analyte, there will be no formation of a sandwich complex, i.e., gold conjugated antibody—analyte—immobilized antibody, and the test line zone 4 will remain colorless as shown in FIG. 5. In the presence of the analyte, the sandwich complex will form on their specific test lines as illustrated in FIGS. 4A-4C. When the gold-antibody conjugate, which is always in excess of the antigens (transferrin and hemoglobin) present in the sample, moves down the membrane and reaches the control line 3, the immobilized goat-anti-mouse IgG will react with the gold-antibody conjugate to form a color line in the control zone 3. The control zone serves as an indicator to assure the liquid movement of the device. The absence of a colored control line as shown in FIG. 6 indicates a failed test.

It should be noted that FIGS. 2-5 are merely illustrations of one test device of the present invention for a simultaneous detection of transferrin and hemoglobin, and are not intended to limit the present invention. For example, those skilled in the art can readily appreciate that the two sites within the test area 4 can also be placed separately (e.g., juxtaposed) at the same position along the lateral flow direction. Furthermore, the test device can be made to contain two separate test strips, one for testing hemoglobin (including a sample pad, a gold-conjugate pad, a test area containing only anti-hemoglobin antibodies and a control area), and the other one for testing transferrin (including a sample pad, a gold-conjugate pad, a test area containing only anti-transferrin antibodies and a control area). With such a device, a user can also have the option to apply the sample to only one of the two test strips, depending on the need and circumstances for the testing.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are possible within the scope of the invention. All the publications mentioned in the present disclosure are incorporated herein by reference.

Example 1

Preparation of Monoclonal Antibodies Against Hemoglobin and Transferrin

BALB/c mice were immunized with purified human hemoglobin for three months to induce antibody production. After the antiserum titer reached a desired level, mice were sacrificed. Isolated spleen cells were used for hybridoma fusion with cells of the SP20 line. A pair of hybridoma cell lines, Hb10E11G12 and Hb2H11D12, were isolated and used to produce ascites fluid from BALB/c mice. Anti-hemoglobin antibodies were then purified from ascites fluid and used in sandwich immunoassays for detecting hemoglobin.

Anti-transferrin antibodies were produced following a similar procedure. A matching pair of hybridoma cell lines, TF31E5G1 and TF32A2G1, were isolated and used in sandwich immunoassays for detecting transferrin.

Example 2

Preparation of Gold Particles and Antibody Conjugate

Antibody-conjugated gold particles were chosen as the detection means in a lateral flow immunoassay. A colloidal gold particle solution was prepared by the reduction of gold chloride with sodium citrate at the boiling point of the mixture. A pink to purple colored colloidal gold solution with gold particles of a size around 10 to 40 nm was used in preparing gold-antibody conjugates. One of the paired antibodies was used to coat gold particles at a pH value close to the pI value of the antibody. BSA and PEG were used to block the leftover binding sites on the gold particles, to wash and concentrate the conjugated gold-antibody solution. A pad, typically a pad made of fiber glass or rayon, was submerged in the conjugated gold-antibody solution and was dried afterwards so that the gold-antibody conjugates were deposited in the pad.

Example 3

Test Lines and Control Line

A nitrocellulose membrane with an average pore size of around 5 to 20 μm was chosen as the test membrane. The selected antibodies were immobilized on the membrane at the specified test line zones. A control line zone was also included in test membrane to assure the physical performance of the test, where a goat anti-mouse-IgG antibody was immobilized.

Example 4

Assembly and Performance of a Test Strip

FIGS. 2-3 illustrate the assembly of a test strip for simultaneous detection of transferrin and hemoglobin based on sandwich immunoassays.

Example 5

Detection of Transferrin

Dilution buffer solutions (typically PBS buffers) in fecal sample collectors were spiked (supplemented with transferrin) to a final concentration of transferrin at 10, 20, 40, 50, 75, and 100 ng/ml, respectively. Three random fecal samples from normal individuals were collected and inserted into collection devices containing transferrin-spiked buffer solutions. These three samples were tested using the test device shown in FIGS. 2-3. The results are shown in Table 1. All sample solutions with a transferrin level above the cutoff value of 30 ng/ml showed a positive signal, and all samples with transferrin below the cutoff value showed negative results.

TABLE 1

| Transferrin (ng/ml) | Sample 1 | Sample 2 | Sample 3 |
|---|---|---|---|
| 10 | − | − | − |
| 20 | − | − | − |
| 40 | + | + | + |
| 50 | + | + | + |
| 75 | + | + | + |
| 100 | + | + | + |

Example 6

Detection of Hemoglobin

Dilution buffer solutions in fecal sample collectors were spiked to a final concentration of hemoglobin at 0.05, 0.1, 0.2, 0.5, 20, and 2000 μg/ml, respectively. Three random fecal samples from normal individuals were collected and inserted into the collection devices containing hemoglobin spiked buffer solutions. These three samples were tested using the test device shown in FIGS. 2-3. The results are shown in Table 2. All sample solutions with a hemoglobin level above the cutoff value of 0.2 μg/ml showed a positive signal and all samples with hemoglobin below the cutoff value showed negative results.

TABLE 2

| Hemoglobin (μg/ml) | Sample 1 | Sample 2 | Sample 3 |
| --- | --- | --- | --- |
| 0.05 | − | − | − |
| 0.1 | − | − | − |
| 0.2 | + | + | + |
| 0.5 | + | + | + |
| 20 | + | + | + |
| 2000 | + | + | + |

Example 7

Differential Diagnosis of Upper GI Bleeding Using Fecal Samples

The hemoglobin and transferrin combination test and a guaiac test were used to assay fecal samples from patients experiencing clinically confirmed stomach problems identified in Table 3. The results of the lateral flow sandwich immunoassay based on the anti-hemoglobin antibodies alone only detected 7 out of 62 cases as positive for fecal blood. The guaiac test, a chemical test that detects the peroxidase activity of heme, identified 25 cases. However, the lack of specificity of the guaiac test made the identification of these 25 cases questionable. On the other hand, the anti-transferrin antibodies identified 51 of 62 cases as positive for fecal blood. Table 3 shows the results. Therefore, transferrin is a more sensitive marker for detection of upper GI bleeding. The combination transferrin and hemoglobin immunoassay permits a differential diagnosis of upper GI bleeding.

TABLE 3

| Symptom | Total Cases | Hemoglobin Test | Guaia Test | Transferrin Test |
| --- | --- | --- | --- | --- |
| Stomach Bleeding | 18 | 6+ | 10+ | 17+ |
| Peptic Ulcer | 5 | 0+ | 2+ | 4+ |
| Ulcer | 14 | 1+ | 5+ | 12+ |
| Operation | 9 | 0+ | 4+ | 6+ |
| Gastritis | 11 | 0+ | 2+ | 9+ |
| Polyp | 5 | 0+ | 2+ | 3+ |

Example 8

Diagnosis of Upper GI Bleeding Using Vomit and Liquid Samples from Upper GI System In this example, seven vomit and stomach fluid samples from clinically confirmed upper GI patients were tested again with the hemoglobin/transferrin combination test device and the guiac test. Results in Table 4 show that all samples were tested negative in the guiac test, and in the immunoassay for hemoglobin as the marker. On the other hand, transferrin tested positive for all samples, indicating occult blood from these upper GI samples.

TABLE 4

| Sample | No. | Hemoglobin | Transferrin | Guaiac test |
| --- | --- | --- | --- | --- |
| Vomit | 4 | All negative | All positive | All negative |
| Stomach fluid | 3 | All negative | All positive | All negative |

Example 9

Diagnosis of Lower Gi Bleeding Using Fecal Samples

Table 5 shows results from a testing of 45 fecal samples from patients with clinically confirmed lower GI disorders. Forty cases where hemoglobin tested positive, transferrin also tested positive. The results also demonstrate that the hemoglobin test and the transferrin test can complement each other to increase the test sensitivity of FOB detection. Either test alone missed a few positive samples, whereas the combination test (which determines FOB based on a positive result from either test) had detected all but two positive samples. The results further demonstrate that the hemoglobin and the transferrin tests are more sensitive than the guaiac test.

TABLE 5

| Sample | No. | Hemoglobin Test | Transferrin Test | Combined Test | Guaiac Test |
| --- | --- | --- | --- | --- | --- |
| Feces | 45 | 40+/5− | 42+/3− | 43+/2− | 16+/29− |

What is claimed is:

1. A lateral flow immunoassay device for simultaneous detection of transferrin and hemoglobin in a sample, comprising a test strip which comprises:
   (1) a sample site for applying said fecal sample;
   (2) a conjugate site downstream of said sample site, wherein a labeled anti-transferrin antibody and a labeled anti-hemoglobin antibody are deposited at said conjugate site;
   (3) a test zone downstream of said conjugate site, wherein said test zone comprises two separate sites, one of which is immobilized with an anti-transferrin antibody, and the other is labeled immobilized with an anti-hemoglobin antibody; and
   (4) a control site wherein a control antibody is immobilized thereto, wherein the test strip is calibrated such that a positive signal appears test site immobilized with said anti-hemoglobin antibody when hemoglobin is present in said sample at higher than the predetermined value of 0.2 μg/ml for hemoglobin, and a positive signal appears in the test site immobilized with said anti-transferrin antibody when transferrin is present in said sample at higher than the predetermined value of 30 ng/ml for transferrin, such that the signals produced from a test sample permit a differential diagnosis of bleeding from the upper GI tract versus the lower GI tract.

2. A lateral flow immunoassay device for simultaneous detection of transferrin and hemoglobin in a sample, comprising two test strips, wherein a first strip comprises:
 (1) a sample site for applying a sample;
 (2) a conjugate site downstream of said sample site, wherein a labeled anti-transferrin antibody is deposited at said conjugate site;
 (3) a test zone downstream of said conjugate site, wherein said test zone comprises a test site wherein an anti-transferrin antibody is immobilized;
 (4) a control site wherein a control antibody is immobilized thereto; and
wherein a second strip comprises:
 (1) a sample site for applying a sample;
 (2) a conjugate site downstream of said sample site, wherein a labeled anti-hemoglobin antibody is deposited at said conjugate site;
 (3) a test zone downstream of said conjugate site, wherein said test zone comprises a test site wherein an anti-hemoglobin antibody is immobilized; and
 (4) a control site wherein a control antibody is immobilized thereto,
wherein the test strips are calibrated such that a positive signal appears in the test site immobilized with said anti-hemoglobin antibody when hemoglobin is present in said sample at higher than the predetermined value of 0.2 μg/ml for hemoglobin, and a positive signal appears in the test site immobilized with said anti-transferrin antibody when transferrin is present in said sample at higher than the predetermined value of 30 ng/ml for transferrin, such that the signals produced from a test sample permit a differential diagnosis of bleeding from the upper GI tract versus the lower GI tract.

3. The device of claim 1 or 2, wherein said test strip comprises a test membrane made of nitrocellulose.

4. The device of claim 1 or 2, wherein said labeled anti-transferrin antibody and said labeled anti-hemoglobin antibody are both antibodies conjugated to gold particles.

* * * * *